(12) United States Patent
Van Rijn et al.

(10) Patent No.: US 6,297,033 B1
(45) Date of Patent: *Oct. 2, 2001

(54) MEANS AND PROCESS FOR NITRATE REMOVAL

(75) Inventors: Jaap Van Rijn; Amos Nussinovitch; Joseph Tal, all of Rehovot (IL)

(73) Assignee: Yissum Research Development Company of the Hebrew University of Jerusalem, Jerusalem (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/952,693

(22) PCT Filed: Apr. 1, 1997

(86) PCT No.: PCT/IL97/00116

§ 371 Date: Mar. 5, 1998

§ 102(e) Date: Mar. 5, 1998

(87) PCT Pub. No.: WO97/37008

PCT Pub. Date: Oct. 9, 1997

(30) Foreign Application Priority Data

Apr. 2, 1996  (IL) ......................................................... 117783

(51) Int. Cl.$^7$ ............................. C12N 11/04; C12N 11/08
(52) U.S. Cl. ......................... 435/182; 435/174; 435/178; 435/262.5; 435/264; 435/268; 435/821; 210/150; 424/461; 424/489; 424/493; 424/494
(58) Field of Search ..................... 435/174, 178, 435/182, 821, 262.5, 264, 268; 210/150; 424/461, 489, 493, 494

(56) References Cited

U.S. PATENT DOCUMENTS

| | | | |
|---|---|---|---|
| 3,607,736 | 9/1971 | Miyaji | 166/246 |
| 4,620,929 | * 11/1986 | Hoffman | 210/610 |
| 5,044,435 | 9/1991 | Sperl et al. | 210/2.11 |
| 5,206,168 | * 4/1993 | Boyle | 435/262 |
| 5,286,495 | 2/1994 | Batich et al. | 424/490 |
| 5,556,536 | * 9/1996 | Turk | 210/150 |

FOREIGN PATENT DOCUMENTS

| | | |
|---|---|---|
| 4028312A1 | 3/1992 | (DE) . |
| 04231056 | * 8/1992 | (JP) . |
| 04231057 | * 8/1992 | (JP) . |
| 05049361 | * 3/1993 | (JP) . |
| 05146629 | * 6/1993 | (JP) . |
| 06025013 | * 2/1994 | (JP) . |
| 8303102 | * 9/1983 | (WO) . |
| 8901034 | * 2/1989 | (WO) . |

OTHER PUBLICATIONS

Hernandez et al., J. Biol. Chem., vol. 263(17), p. 7937–39, 1988.*

Rueger, Veroeff Inst. Meeresforsch BremerLauen, vol. 21(1), p. 97–114, 1985.*

Nussinovitch et al., Biotechnol. Prog., vol. 12(1), P. 26–30, 1996.*

XP–002151212, HU 211390, Feb. 1996, Kalman et al.

* cited by examiner

*Primary Examiner*—Chhaya D. Sayala
(74) *Attorney, Agent, or Firm*—Eitan, Pearl, Latzer & Cohen-Zedek

(57) ABSTRACT

A system for nitrate removal from aquariums, both fresh water and marine aquariums, by means of permeable polymeric beads which contain a combination of fermentative and denitrifying bacteria and a carbon source. Preferred beads are beads made from sodium alginate or chitosan. The bacteria, in the presence of the carbon source, are able to reduce nitrate to nitrogen gas. Bacteria which are not harmful to fish are used. The porous beads used in the process are novel and part of the invention.

18 Claims, 2 Drawing Sheets

MEANS AND PROCESS FOR NITRATE REMOVAL

FIELD OF INVENTION

A system for nitrate removal from aquariums by means of novel porous beads. These contain a combination of fermentative bacteria, denitrifying bacteria and a suitable carbon source. Preferred beads are beads of sodium alginate or chitosan. There is provided a system based on the use of such beads where the aquarium is connected with ammonia removal means and nitrate removal means.

BACKGROUND

Control of water quality in both freshwater and marine aquariums is usually conducted by means of filtration systems. These filtration systems comprise mechanical filtration means for organic material and means for the biological conversion of ammonia to nitrate by immobilized nitrifying bacteria. Nitrate, the end product of nitrification, accumulates in the water and is usually not removed.

With the booming interest in the aquarium hobby and, consequently, the introduction of new exotic ornamental fish species, higher demands are set with regard to the water quality in aquariums. Much of the recent literature in this field stresses the need for nitrate removal for several reasons:

1. some ornamental fish species are unable to propagate or grow in water containing high nitrate levels (e.g. softwater fish species such as discus, marine fish species).
2. high nitrate levels in aquariums stimulate undesired algal growth on the walls of the aquaria (fouling).

Until a few years ago no systems for nitrate removal from aquariums were commercially available and nitrate concentrations were controlled by periodical dilution of the aquarium water with clean water. Today, only a limited number of commercial biofiltration systems tuned at nitrate removal from aquariums are available.

These filters are based on the principle of creating conditions which stimulate growth of denitrifying bacteria that reduce nitrate to nitrogen gas. Conditions for the growth of these denitrifying bacteria are:

1) the absence of oxygen,
2) the presence of a degradable organic carbon source to serve as feed for denitrifiers.

Unlike filters used for ammonia removal, the performance of denitrifying filters is often erratic and their successful use largely depends on the skills and experience of the operator. Specifically, it is often difficult to pass water to be treated through an anoxic, denitrifying zone without causing oxygen enrichment of this zone. Furthermore, addition of a carbon source is most difficult to balance: Too much carbon addition will cause a wash-out and pollution of the aquarium water whereas too little carbon will lead to incomplete denitrification and often to accumulation of toxic nitrite.

Considering the existing need for nitrate removal from aquariums and, furthermore, problems encountered with the few commercially-available filters for nitrate removal, it can be concluded that a need exists for denitrifying filters that are easy to operate and bring about a rapid removal of nitrate from aquariums.

The novel polymeric beads of the present invention can also be used for the removal of excess nitrate content form various effluents and from any aqueous medium having too high a nitrate content.

DESCRIPTION OF THE INVENTION

Figure 1:
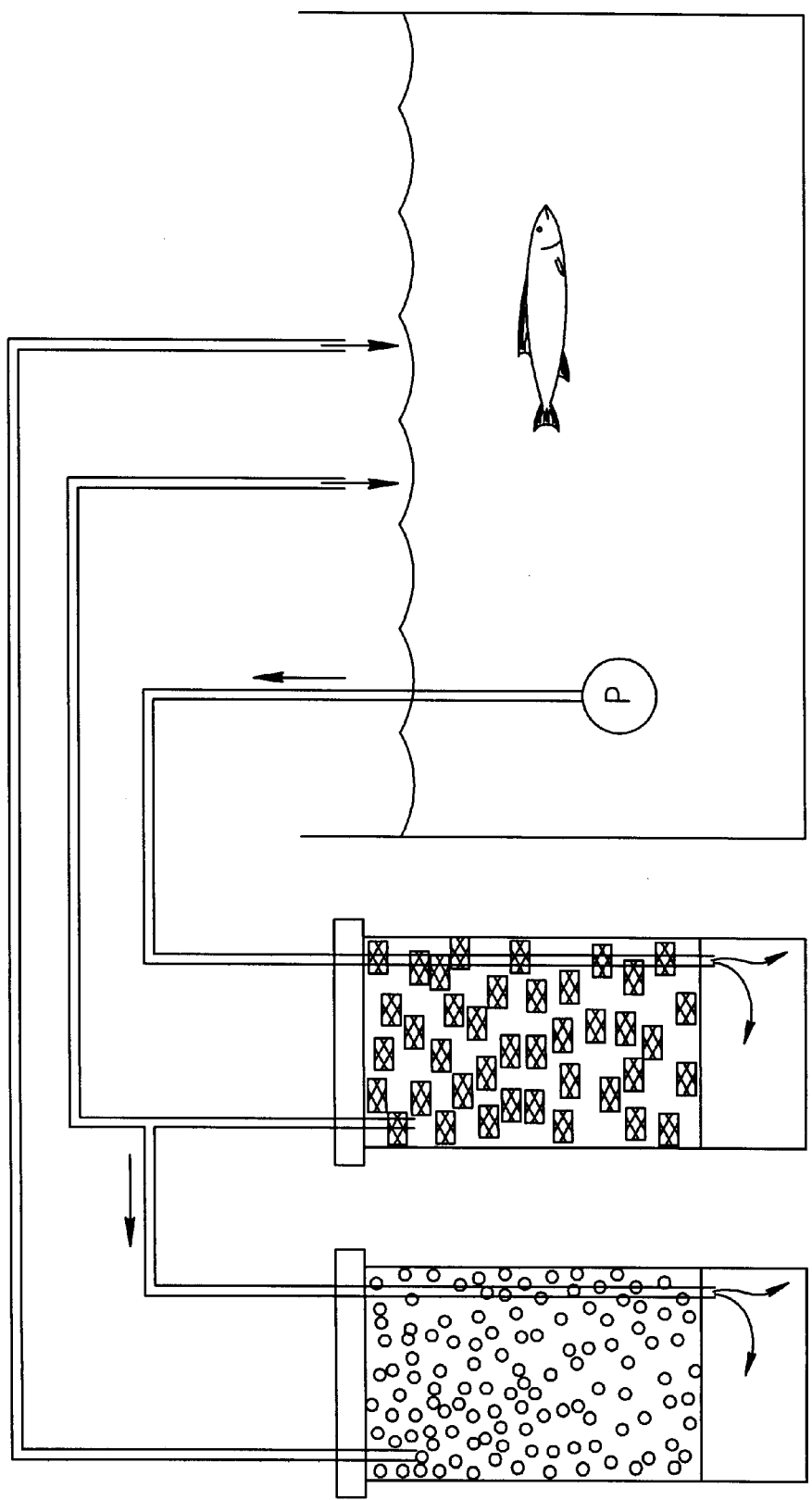
FIG. 1 is a schematical side view, not according to scale, of an aerobic and anaerobic aquarium water filtration and nitrate removal system.

The invention is based on polymer-entrapment of a denitrifying combination of bacteria together with a suitable carbon source which is slowly degraded by a combination of two different bacteria. The bacteria comprise of a combination of denitrifying and fermentative bacteria which, when entrapped in a suitable polymer and in the presence of an organic carbon source, are capable of reducing nitrate to nitrogen gas without intermediate accumulation of toxic metabolites (e.g. nitrite). Various bacterial strains for this combination were isolated in our laboratory and are non-pathogenic to fish. The natural (non-toxic) polymers chitosan and alginate advantageously are used for entrapment of the bacteria. The final product are porous beads of approximately 3 mm diameter, comprising of the polymer and the entrapped bacterial combination and carbon source. The carbon source can be starch, cellulose or another degradable high molecular weight source of carbon. A certain amount of beads (depending on the size and the amount of fish present in the aquarium) are placed in a closed vessel receiving water from the aquarium at a rate of several ml per minute. The beads-containing vessel is placed on-line with any commercially-available aerobic biofilter and thus there is no need for an additional pump (see FIG. 1). Products of one of the bacteria serves as nutritional source for the other bacterial type.

Preliminary Results

Figure 2:
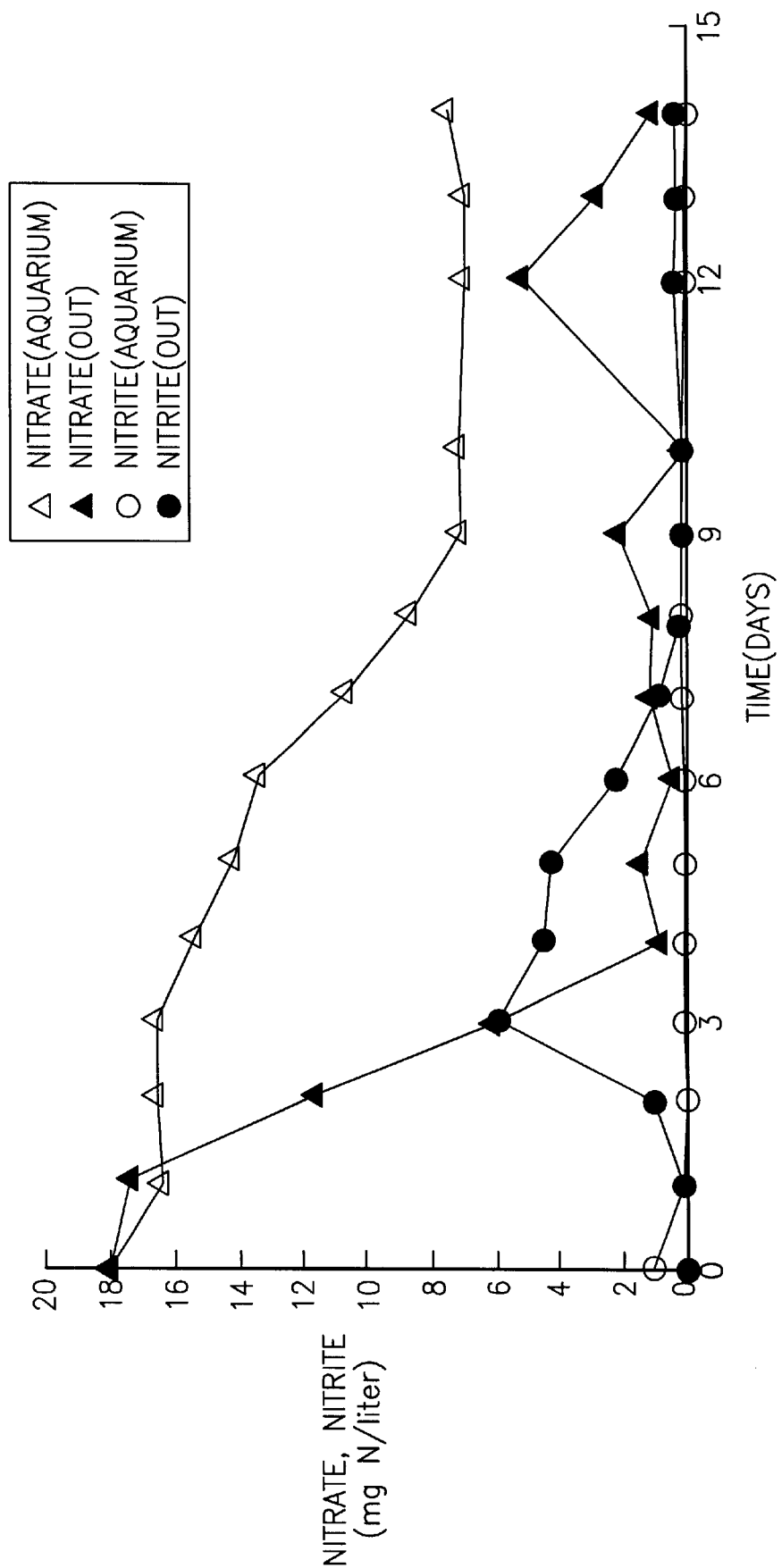
FIG. 2 is a graphic presentation of nitrite and nitrate concentrations in an aquarium during a period of 15 days.

Changes in mechanical, structural and biological properties of chitosan-entrapped *Pseudomonas stutzeri* (a denitrifying bacterium) was recently described (Nussinovitch et al., 1995). Incubating this complex under denitrifying conditions in the presence of an external carbon source resulted in nitrate removal rates, comparable to removal rates of non-entrapped bacteria. Additional studies conducted in the laboratories of the authors revealed that even higher nitrate removal rates could be obtained by combined entrapment of such a *P. stutzeri* strain and a *B. pumilus* strain. In the latter studies, chitosan was substituted by sodium-alginate and instead of external addition, the carbon source (either starch or cellulose) was incorporated into the beads. Based on this, alginate beads were prepared containing starch (0.1%), *P. stutzeri* and *Bacillus pumilus*. The beads were incubated in a vessel which was placed on-line with a commercially-available aerobic filter (Eheim, Germany, model: 2213). Both filters were connected to a 100-liter aquarium containing approximately 200 gram of ornamental fish. The configuration of aquarium and biofilters is presented in FIG. 1. The fish were fed daily at saturation (approximately 1% of total body weight) with commercially-available feed flakes (Europe Flaks, Kintz Fish Food Co. Taiwan). During a start-up period of two weeks, daily concentrations of ammonia, nitrite and nitrate were recorded in the aquarium and at the outlet of the anaerobic filter. In the aquarium water, nitrate levels decreased from 18 mg to around 8 mg $NO_3$-N /liter within the first 4 days, whereas nitrite was only detectable on the first day. During the first 7 days, nitrite was produced during the anaerobic filtration process. Very low levels of nitrate in the outlet of the anaerobic filter were detected from day 4 onward (FIG. 2). Ammonia concentrations were below detectable levels both in the aquarium and at the outlet of the anaerobic filter. After approximately 4 weeks (not shown) nitrate removal by the anaerobic filter ceased due to a depletion of the carbon source in the beads. The mechanical properties of the beads was examined and it was found that, although some deformation and weakening of the beads occurred, very few beads were disrupted at the end of the 4-week period.

Through follow-up studies (not shown) it was found that the denitrification potential of the beads could be extended significantly by addition of larger quantities of starch (up to 15% of the bead weight) or by substituting the starch by cellulose. Although, as compared to starch, incorporation of cellulose resulted in slower nitrate removal rates, the period of nitrate removal by the beads was significantly extended.

EXAMPLE 1

Sodium alginate was dispersed in water to give a concentration of from about 0.3% and up to about 4%. Double-distilled water was used at room temperature for the dissolution. Higher concentrations are required if higher concentrations of bacteria are to be entrapped, and one has to take into consideration also their concentration after cultivation. During the dissolution of the sodium alginate, starch is added, at a quantity of 0.2 to about 33 weight-% and denitrification bacteria are added at a concentration from about $10^2$ to about $10^8$ per ml, in addition fermentative bacteria, are added at a concentration in the range from $10^2$ to about $10^3$ per ml. The resulting dispersion is added dropwise to a calcium chloride solution of from about 0.2 to about 10 weight-%, resulting in beads of different mechanical properties. The resulting beads are frozen by means of liquid nitrogen and freeze dried. The resulting alginate sponges are used for denitrification purposes of aqueous media, such as aquarium water.

EXAMPLE 2

Sodium alginate beads containing about $10^7$ *Pseudomonas* bacteria and about $10^5$ fermentative bacteria were produced as set out in Example 1. The resulting beads were introduced in a wet state into a chitosan solution (1 to 15 weight-%) which was previously brought to a neutral pH. After 3 hours of immersion the beads were removed and freeze dried.

EXAMPLE 3

Beads according to example 1 were immersed in a polylysin solution, in a polyarginin solution or in sodium hexametaphosphate, and subsequently freeze dried, resulting in increased mechanical strength.

EXAMPLE 4

Sodium bicarbonate (0.1–2.5 weight-%) was added to a dispersion similar to that described in example 1. The resulting beads were introduced into a dilute solution of 0.5% citric acid for about 10 minutes. Liberation of gas and its diffusion through the polymer resulted in an increased porosity of the bead. A further increase in porosity was obtained by subsequent freeze drying which was performed as described in example 1.

EXAMPLE 5

Either sodium sorbate (1000 ppm) or sodium benzonate (500 ppm) were added as preservation agents to prevent fungal and yeast growth to a solution as described in example 1.

EXAMPLE 6

After preparation beads were packaged in plastic (polythene) bags in air, in nitrogen or in carbon dioxide or under vacuum, at a minimum humidity. Such packaging prevents deterioration during storage.

EXAMPLE 7

To a dispersion according to Example 1, there was added instead of starch another high M.W. compound, such as cellulose, a hydrocolloid or other substance which undergoes fermentation by means the of the bacteria used resulting in assimable nutrients for the denitrification bacteria.

What is claimed is:

1. Permeable denitrifying polymeric beads comprising:
    a polymer or combination of polymers,
    a fermentative bacteria,
    a denitrifying bacteria, and
    starch,
    wherein said fermentative bacteria, said denitrifying bacteria and said starch are entrapped within said permeable polymeric beads, wherein said starch is incorporated into the beads and serves as a nutrient for said bacteria, wherein the product of the fermentative bacteria serves as a nutritive source of the denitrifying bacteria, and wherein said beads are dried.

2. Permeable beads of claim 1, wherein the fermentative bacteria are of the Bacillus genus.

3. Permeable beads of claim 2, wherein the fermentative bacteria are of the Bacillus pumilus species.

4. Permeable beads of claim 1, wherein the denitrifying bacteria are of the Pseudomonas genus.

5. Permeable beads of claim 4, wherein the denitrifying bacteria are of the Pseudomonas stutzeri species.

6. Permeable beads of claim 1, wherein the denitrifying bacteria are of the Pseudomonas genus and the fermentative bacteria are of the Bacillus genus.

7. Permeable beads of claim 6, wherein the denitrifying bacteria are of the Pseudomonas stutzeri species and the fermentative bacteria are of the Bacillus pumilus species.

8. Permeable beads of claim 1, wherein the polymer is selected from the group consisting of chitosan, alginate or a gelling agent which undergoes setting at room temperature.

9. Permeable beads of claim 1, wherein the beads have an average size from about 1 to about 5 mm diameter.

10. A process for the denitrification of an aqueous medium containing an excess of nitrates or nitrites, comprising the steps of:
    applying said medium to permeable denitrifying dried polymeric beads according to claim 1, and
    denitrifying said aquoes medium coming in contact with said denitrifying bacteria.

11. A process of claim 10, wherein the aqueous medium is aquarium water.

12. A process of claim 10, wherein the aqueous medium is waste water.

13. A process of claim 10, wherein the aqueous medium is applied to a bed of said permeable polymeric beads.

14. A method of making a permeable denitrifying dried polymeric bead of claim 1, comprising:
    dispersing a polymer or combination of polymers in an aqueous medium;
    adding starch to said dispersion;
    adding denitrifying bacteria to said dispersion;
    adding fermentative bacteria to said dispersion;
    adding the resultant dispersion mixture dropwise to a calcium chloride solution to form beads; and
    freeze drying the formed beads;
    whereby said fermentative bacteria, said denitrifying bacteria and said starch are entrapped within said permeable polymeric beads, wherein said starch is incorporated into the beads and serves as a nutrient for said bacteria, wherein the product of the fermentative bacteria serves as a nutritive source of the denitrifying bacteria.

15. A process for the denitrification of water from an aquarium containing an excess of nitrates or nitrites, comprising:
- placing the permeable denitrifying dried polymeric beads of claim 1 in a closed vessel capable of receiving said water from the aquarium;
- receiving said water from the aquarium into the closed vessel;
- applying said water to the permeable denitrifying dried polymeric beads;
- denitrifying said water coming in contact with said denitrifying bacteria; and
- returning denitrified water back to the aquarium.

16. A system for removal of nitrate comprising:
- a fermentative bacteria,
- a denitrifying bacteria,
- starch, and
- permeable polymeric beads, comprising a polymer or combination of polymers in which said fermentative bacteria, said denitrifying bacteria and said starch are entrapped within said permeable polymeric beads, wherein said starch is incorporated into the beads and serves as a nutrient for said bacteria, wherein the product of the fermentative bacteria serves as a nutritive source of the denitrifying bacteria, and wherein said beads are dried.

17. An aerobic and anaerobic aquarium water filtration and nitrate removal system for an aquarium comprising:
- an aquarium
- an aerobic biofilter, and
- an anaerobic biofilter which comprises:
  a system according to claim 16.

18. Permeable denitrifying polymeric beads comprising:
- a polymer or combination of polymers,
- a fermentative bacteria selected from the Bacillus genus,
- a denitrifying bacteria selected from the Pseudomonas genus, and
- starch, wherein said fermentative bacteria, said denitrifying bacteria and said starch are entrapped within said permeable polymeric beads, wherein said starch is incorporated into the beads and serves as a nutrient for said bacteria, wherein the product of the fermentative bacteria serves as a nutritive source of the denitrifying bacteria, and wherein said beads are dried.

* * * * *